United States Patent
Phua et al.

(10) Patent No.: US 7,008,132 B1
(45) Date of Patent: Mar. 7, 2006

(54) SURGICAL SCRUB APPLIANCE

(75) Inventors: Swee Hoe Phua, Singapore (SG); Wai Chiau Kwok, Singapore (SG); Soei Kiat Yap, Singapore (SG)

(73) Assignee: Inzign PTE LTD, Singapore (SG)

( * ) Notice: Subject to any disclaimer, the term of this patent is extended or adjusted under 35 U.S.C. 154(b) by 0 days.

(21) Appl. No.: 10/275,514

(22) PCT Filed: May 4, 2000

(86) PCT No.: PCT/SG00/00061

§ 371 (c)(1),
(2), (4) Date: Apr. 1, 2003

(87) PCT Pub. No.: WO01/82762

PCT Pub. Date: Nov. 8, 2001

(51) Int. Cl.
*A46B 11/00* (2006.01)
*A47L 13/26* (2006.01)
*B05C 1/00* (2006.01)

(52) U.S. Cl. .................. 401/125; 401/139; 401/16; 401/17; 401/27; 401/38; 401/39

(58) Field of Classification Search ............... 401/139, 401/16, 27, 38, 39, 125, 17, 18, 23, 24, 36, 401/37, 44, 47, 6, 206, 133, 132; 215/309, 215/310, 230, 235, 236, 306, 317; 139/92
See application file for complete search history.

(56) References Cited

U.S. PATENT DOCUMENTS 2,209,544 A * 7/1940 Seeberger .................... 401/23
3,574,312 A * 4/1971 Miller ....................... 138/96 R
3,966,335 A 6/1976 Abramson .................... 401/10
D285,627 S 9/1986 Ballard ........................ D4/120
4,730,949 A 3/1988 Wilson ........................ 401/132
4,859,102 A * 8/1989 Chamieh ..................... 401/17
5,014,866 A * 5/1991 Moore ........................ 215/364
5,035,468 A * 7/1991 Brown et al. ................. 300/21
5,312,197 A * 5/1994 Abramson ..................... 401/6
5,865,353 A * 2/1999 Baudin .................... 215/235 X
6,682,246 B1 * 1/2004 Reggiani .................... 401/264
6,720,044 B1 * 4/2004 Andersson et al. ........ 428/35.7

FOREIGN PATENT DOCUMENTS

| CN | 2079946 U | 7/1991 | |
|----|-----------|--------|--|
| CN | 2185687 Y | 12/1994 | |
| GB | 2125280 | 3/1984 | |
| JP | 08040462 A * | 2/1996 | ................. 215/235 |
| TW | 88218566 | 11/1999 | |

OTHER PUBLICATIONS

International Search Report of PCT/SG00/00061 dated Mar. 29, 2001.
Taiwanese Office Action with English language translation dated Sep. 27, 2002.

* cited by examiner

Primary Examiner—David J. Walczak
(74) Attorney, Agent, or Firm—Ostrolenk, Faber, Gerb & Soffen, LLP

(57) ABSTRACT

A surgical scrub appliance is disclosed having a rigid housing (10) to which a sponge (20) is connected, the housing forming at least one container (30, 40) for liquid, the container having a sealable opening.

13 Claims, 4 Drawing Sheets

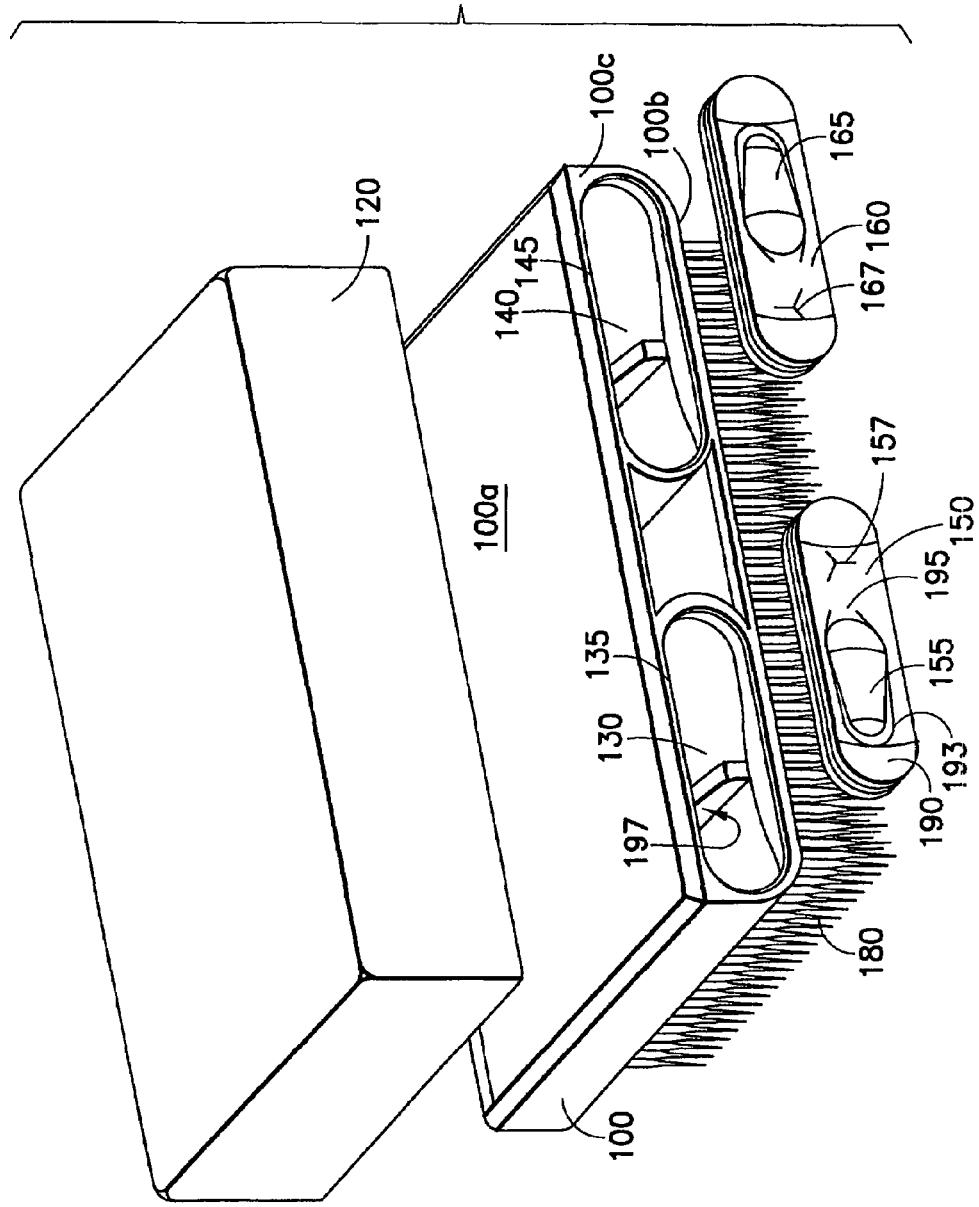

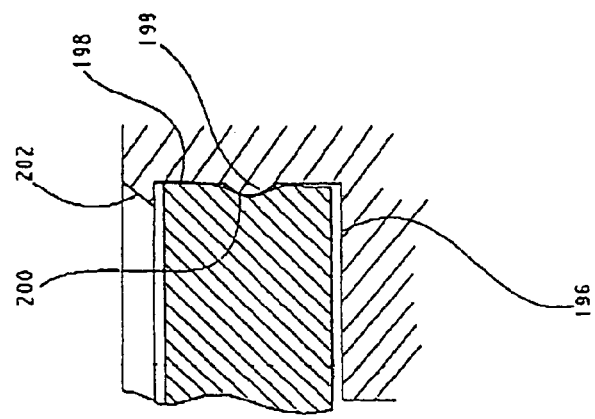
FIG. 5b
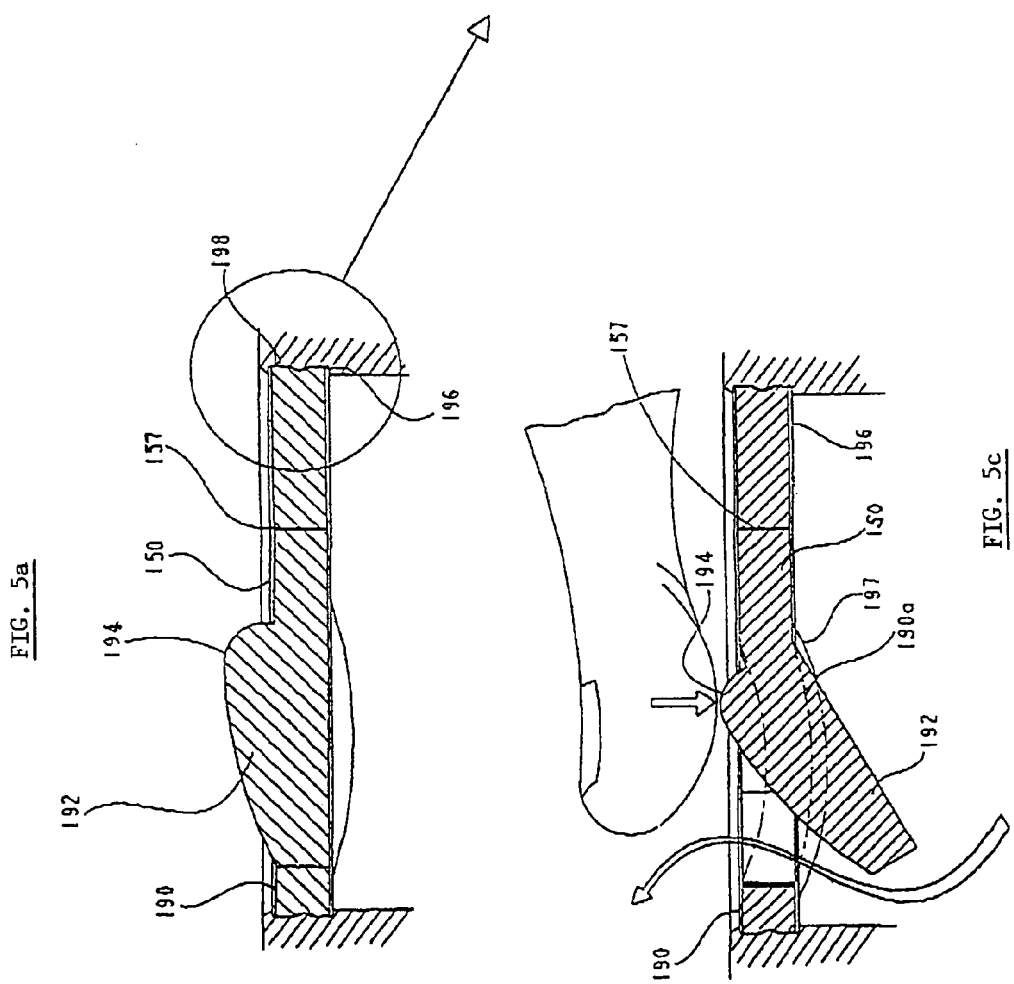
FIG. 5a
FIG. 5c

SURGICAL SCRUB APPLIANCE

BACKGROUND AND FIELD OF THE INVENTION

This invention relates to a surgical scrub appliance.

Before conducting an operation, surgical staff are required to "scrub up". This involves carefully and thoroughly washing the hands and arms up to the shoulder. Conventionally, dispensers of soap or other cleaning solutions have been provided for this purpose. However, the act of using a dispenser can be a cause for contamination. Furthermore, the dispenser requires refilling and general servicing usually needing a contract with an outside firm leading to expense.

Proposals have been made, for example in U.S. Pat. No. 5,312,197 and U.S. Pat. No. 4,730,949 to provide surgical scrub brushes which includes a supply of antiseptic soap or other cleansing liquid. In U.S. Pat. No. 5,312,197 the cleansing liquid is provided in an independent chamber to one side of the scrubbing brush. In U.S. Pat. No. 4,730,949, the soap is provided in a reservoir between a sponge and a housing to which the sponge is connected. Both proposals have the disadvantage that they are expensive to manufacture, with a separate independent member needing to be connected to the surgical brush of U.S. Pat. No. 5,312,197 and an internal reservoir being provided in U.S. Pat. No. 4,730,949. The presence of this internal reservoir also makes it very difficult to attach the sponge to the housing in a secure manner. Furthermore, in both these proposals, a single reservoir is provided although it is necessary to wash both arms with a single surgical scrubbing brush and it is difficult for the user to assess how much soap has/is able to be used for the first arm while leaving enough for the second.

It is an object of the invention to provide a surgical scrub appliance which alleviates at least one of the disadvantages of the prior art noted above.

SUMMARY OF THE INVENTION

According to the invention there is provided a surgical scrub appliance comprising a support to which a sponge is connected, the support forming at least one container for liquid, the container having a sealable opening.

Since the container is formed as part of the support, the container contributes to the overall structure of the appliance.

The support may be rigid.

In one preferred form, the opening may be sealed by a plug. In another preferred form, the opening is sealed by an elastomeric member with the elastomeric member preferably including a resealable dispensing opening and a resealable filling opening.

Most preferably, the appliance further comprises a second container for liquid formed in the housing, the second container having a sealable opening which in a preferred form may be sealed by any of the techniques noted above.

BRIEF DESCRIPTION OF THE DRAWINGS

Embodiments of the invention will now be described, by way of example, with reference to the accompanying drawings in which:

FIG. 4 is an exploded three dimensional view of a second embodiment of the surgical scrub appliance of the invention; and FIGS. 5a–c are cross sectional three views of an elastomeric sealing member of the embodiment.

DETAILED DESCRIPTION OF THE PREFERRED EMBODIMENT

Figure 1:
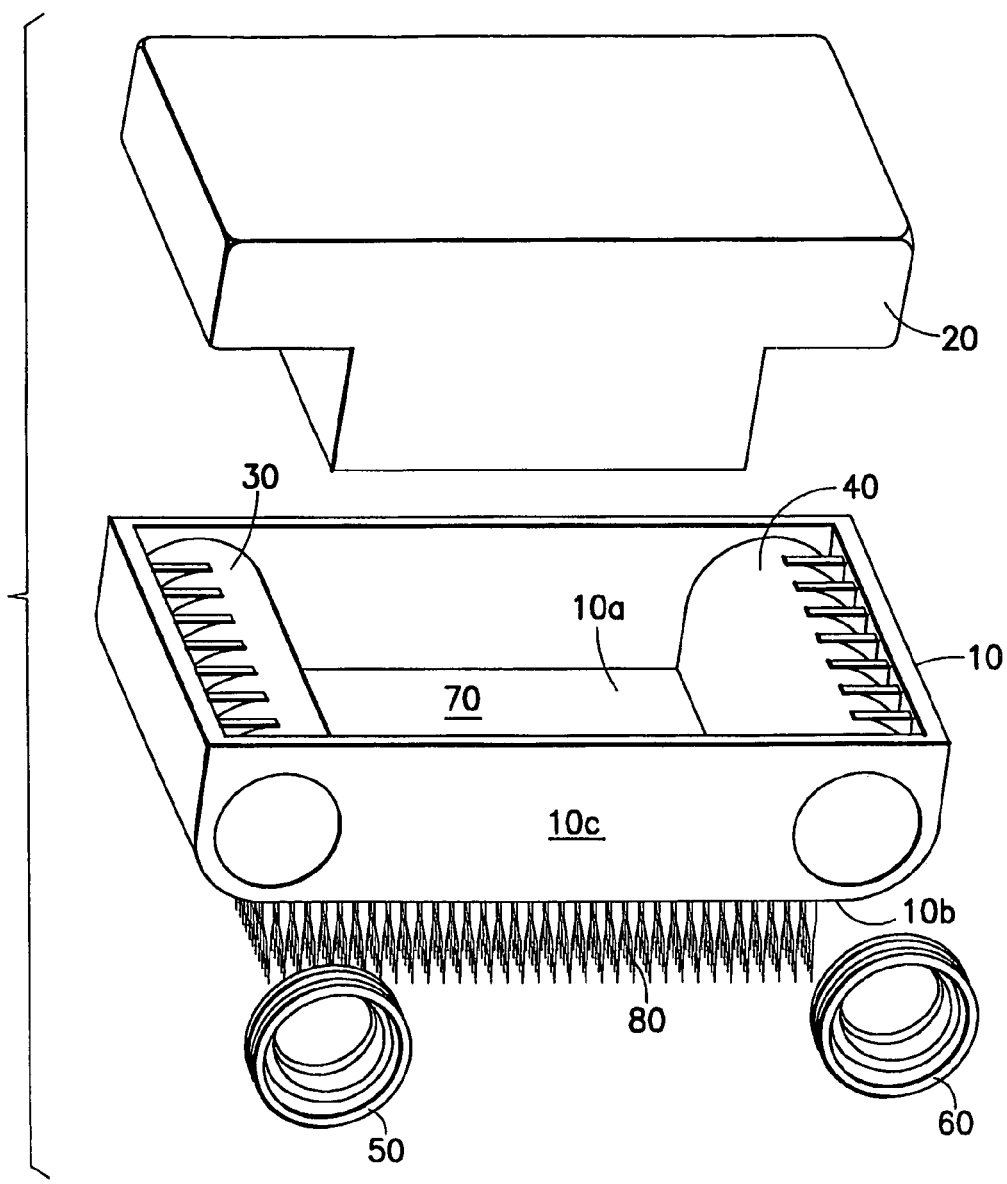
FIG. 1 is an exploded three dimensional view of a first embodiment of the surgical scrub appliance of the invention.
Figure 3:
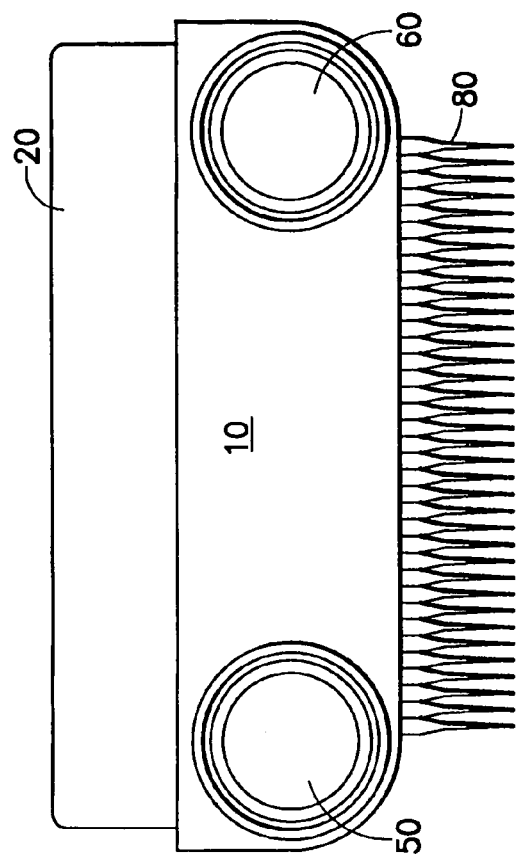
FIGS. 2 and 3 are respectively a front view and side view of the brush of FIG. 1 (unexploded)
Figure 2:
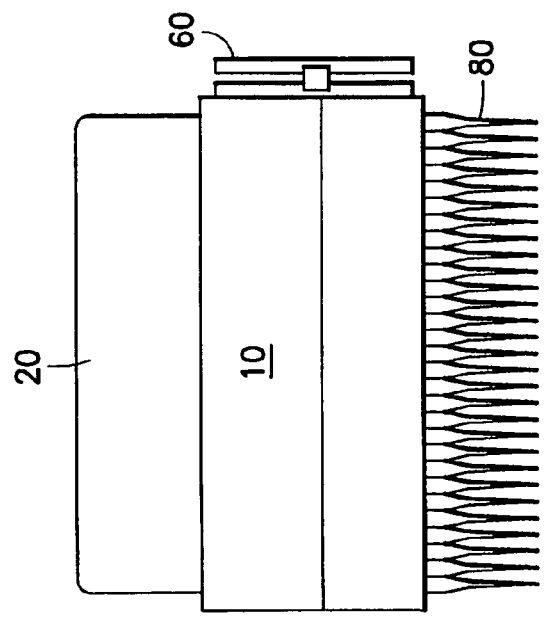

With reference to FIGS. 1–3 the first embodiment of the invention is shown which comprises an injection molded plastics support 10 having a first surface 10a to which a sponge 20 made of foam material is connected by an adhesive. The support 10 is formed by injection moulding from rigid or tough but flexible plastics material and is provided with a base 70 and two containers or cavities 30, 40 which in use are filled with a liquid used during the surgical scrub procedure, for example an antiseptic skin cleanser such as Alphcidine scrub or skin conditioner. Each cavity 30, 40 is sealed by a plug 50, 60. On a second surface 10b of the support 10, which is an outward facing surface of the base 70 of the support 10, a brush 80 is formed integral with the base 70.

In use, the surgeon, when scrubbing up, removes one cap 50 and uses the liquid therein to wash one arm. When he has finished, he grasps the appliance in that arm and removes the cap 60 of the second cavity 40 and then scrubs up that arm using the liquid in cavity 40.

Since the cavities 30, 40 are formed as part of the support 10, they contribute to the overall structure of the appliance and at the same time provide a firm surface to which the sponge 20 may be attached. As shown in FIG. 1, the openings of the cavities 30, 40 are disposed in a third surface 10c of the support 10.

A second embodiment of the invention is shown in FIGS. 4 and 5 and comprises an injection molded support 100 to which a sponge 120 is attached to a surface 100a by an adhesive. Two cavities 130, 140 are formed in the support and are fillable, like the embodiment of FIGS. 1–3 with liquid such as antiseptic skin cleaner. Each cavity 130, 140 is provided with an opening 135, 145 disposed on another surface 100c of the support 100 and in which an elastomeric member 150, 160 is sealably fitted. Each member 150, 160 is provided with two openings, a dispensing opening 155, 165 and a filling opening 157, 167. A brush 180 is integrally connected to the housing in the manner of the embodiment of FIGS. 1–3 (i.e., the brush 180 is connected to yet another surface 100b of the support 100).

FIGS. 5a–5c show the dispensing operation of elastomeric member 150 with FIG. 5a showing a cross sectional view through opening 135 with elastomeric member 150 in place, FIG. 5b being a close up of an edge of the elastomeric member showing how this is sealed against the support 100. FIG. 5c is similar to FIG. 5a showing a dispensing operation.

The elastomeric member 150 includes a peripheral support portion 190. A movable sealing flap 192 is separated from the support portion 190 by a slit 193 formed on three sides of the flap 192 and is joined to support portion 190 by means of a bridge portion 195, as shown in FIG. 4. The sealing flap 192 effects a seal against support portion 190 along slit 193 when in the position shown in FIGS. 4 and 5a. This seal may be augmented by applying a sealing tape or such like over the portion 192 if required. The flap 192 has a finger actuation projection 194. The support portion rests upon a peripheral lip 196 of the opening 135. The lip 196 is flat apart from two opposed arcuately recessed portions 197.

The peripheral side 198 of the opening 135 adjacent the lip 196 is provided with a bead 199 which engages with a peripheral hollow 200 of the member 150. At one end of side 198, a further lip 202 is provided to retain the elastomeric member 150 in place. The portion of the elastomeric member 150 below bead 199 is also a slight interference fit in opening 135 to improve the sealing effect, with the portion of the elastomeric member 150 above bead 199 being a snug non-interference fit.

In use, as shown in FIG. 5c, the thumb of the user engages the finger actuation projection 194 causing the sealing flap 192 to be depressed thus allowing liquid to escape from the container 130. The arcuate recessed portion 197 of lip 196 allows part 190a of the support portion 190 to also be depressed allowing a larger opening for liquid than would otherwise be the case.

The filling openings 157, 167, which are in the form of star-shaped slits allow a filling member to be inserted into the cavities 130, 140 after the elastomeric members 150, 160 have been fitted in place in openings 135, 145. When the filling member is withdrawn, the filling opening closes behind it thus sealing the cavity. This provides advantages in mass production of the brush since the cavities to be filled after the elastomeric members have been fitted, leading to a much cleaner filling method.

The embodiments of the invention as described are not to be construed as limitative. For example, the cavities may be sealed by any other convenient means, for example using a metal foil seal in the manner of a yogurt pot. Furthermore, only a single cavity or more than two cavities may be provided depending on need. Furthermore, the cavities may be filled with the same liquid, for example, soap, disinfectant or skin conditioner or may be filled with different liquids depending on need. The sealing means for the cavities may be colour coded.

What is claimed is:

1. A surgical scrub appliance comprising a support having a first surface to which a sponge is connected and a second surface to which a brush is connected, the support forming at least one container for liquid, the container having a sealable opening disposed in a third surface to which neither the brush nor the sponge is connected, the appliance further comprising means for sealing the opening which includes an elastomeric member having a sealable dispensing opening.

2. An appliance as claimed in claim 1 wherein the support is rigid.

3. An appliance as claimed in claim 1 wherein the elastomeric member has a movable flap sealing the dispensing opening.

4. An appliance as claimed in claim 1 wherein the elastomeric member includes a resealable filling opening.

5. An appliance as claimed in claim 1 wherein the support includes a lip upon which the elastomeric member is disposed.

6. An appliance as claimed in claim 5 wherein the lip is recessed away from the elastomeric member in at least one region adjacent the dispensing opening.

7. An appliance as claimed in claim 1 wherein the opening has a peripheral side with a bead adapted to engage the elastomeric member.

8. An appliance as claimed in claim 7 wherein the elastomeric member includes a portion which is an interference fit in the opening.

9. An appliance as claimed in claim 8 wherein the portion lies to one side of the bead.

10. An appliance as claimed in claim 1 wherein the support forms at least one further container for liquid having a sealable opening.

11. An appliance as claimed in claim 10 wherein the openings are sealed with respective colour coded sealing means.

12. An appliance as claimed in claim 1 wherein the brush is formed as part of the support.

13. A surgical scrub appliance comprising
   a support to which a sponge is connected, the support forming at least one container for liquid; the support having first, second and third surfaces; the container having a sealable opening arranged to be sealed by an elastomeric member;
   an elastomeric member to be sealingly received in the sealable opening in the container;
the elastomeric member includes a sealable dispensing opening;
   the sponge is connected to the first surface of the support;
   a brush connected to a second surface of the support; and
   the sealable opening is disposed in the third surface of the support to which neither the brush nor the sponge is connected.

* * * * *